United States Patent [19]

Revel et al.

[11] Patent Number: 4,622,292
[45] Date of Patent: Nov. 11, 1986

[54] ASSAY AND KIT FOR DETERMINING INTERFERON

[75] Inventors: Michel Revel; David Wallach, both of Rehovot, Israel

[73] Assignee: Yeda Research and Development Company Ltd., Rehovot, Israel

[21] Appl. No.: 525,618

[22] Filed: Aug. 22, 1983

[30] Foreign Application Priority Data

Sep. 7, 1982 [IL] Israel .......................................... 66733

[51] Int. Cl.$^4$ ................... G01N 33/53; G01N 33/545; G01N 33/60
[52] U.S. Cl. ............................................ 435/5; 435/7; 435/810; 436/531; 436/804; 436/808; 436/828
[58] Field of Search ............... 435/5, 7, 810; 436/531, 436/804, 808, 828

[56] References Cited

PUBLICATIONS

Julkunen, I. et al., J. Virol. Methods, 5(2), 85–91 (1982).
Lyons, S. F. et al., J. Virol. Methods, 5(2), 93–100 (1982).

Primary Examiner—Sidney Marantz
Attorney, Agent, or Firm—Browdy and Neimark

[57] ABSTRACT

An assay and kit for the detection and quantitative determination of interferon. The assay is based on the exposure of certain cells to a solution containing the interferon which is to be determined, infecting the cells with a certain virus, incubating for a predetermined period of time, lysing the infected cultures and determining the virus protein. The measurement of the virus proteins can be effected by ELISA or radioimmunoassay.

15 Claims, 13 Drawing Figures

ASSAY AND KIT FOR DETERMINING INTERFERON

SUMMARY OF THE INVENTION

The present invention relates to an assay for the detection and the quantitative determination of interferon (IFN) by measuring the yield of viral proteins in cells treated with the IFN and infected with a suitable virus, using an immunoassay (either ELISA or radioimmunoassay); and a kit for carrying out such an assay.

BACKGROUND OF THE INVENTION

The interferons (IFNs) are proteins which inhibit, specifically, the growth of viruses in cells. The 'antiviral' effect of the IFNs is exhibited by minute ($10^{-13}$M) IFN concentration and therefore most assays for IFN are based on the quantitation of this effect.

Since the direct quantitation of virus yield by the 'plaque assay' is too laborious to be applied as an assay for IFN, a variety of alternative techniques has been developed. In most cases the virus yield is estimated indirectly by determining the extent of cell destruction by the virus.

This technique has several severe limitations: not in all types of cells is the viral cytopathic effect clear enough to be easily estimated and many other agents, besides viruses, can increase cell death and can, therefore, interfere with this 'cytopathic effect' assay of IFN.

Other techniques which are used for estimation of the antiviral effect are based on quantitation of various other viral functions including certain viral enzymatic activities and hemagglutination activity of viruses. These techniques can be used only for those viruses which exhibit the measured activity and are therefore applicable only with limited cell-virus combinations.

A more general technique which makes possible the direct quantitation of viral components, in an accurate and sensitive manner, is, therefore, necessary for a reliable determination of IFN.

BRIEF DESCRIPTION OF THE INVENTION

The present invention relates to an assay for the determination of IFN. It is based on a simple solid-phase immunoassay for viral proteins such as those of Vesicular Stomatitis Virus (VSV), a virus which is widely used to probe for the antiviral activity of IFN. It has been found that the proteins of this virus bind effectively to suitable supports such as polyvinyl-chloride (PVC) surfaces, even in the presence of a high level of other proteins, such as those found in the growth media used for tissue-culture. The accessibility of viral proteins to such binding can be highly increased by lysing the virus with suitable detergent. A simple immunoassay for the viral proteins can therefore be performed by adding a detergent to a virus infected cell culture and applying the detergent-treated solution to PVC microwells. The amount of viral proteins which binds to the PVC is directly proportional to their concentration in the culture. The bound proteins can be quantitated by incubating the microwells with anti-VSV antibody and then measuring the amount of adsorbed IgG. The decrease of VSV protein in interferon (IFN)-treated cultures is correlated with inhibition of formation of infectious virions; its quantification therefore allows accurate measurement of IFN and of its antiviral effect, FIG. 3. The applicability of the immunoassay for measuring the virus yield is not restricted to cells exhibiting a virus cytopathic effect. Moreover, the decrease of virus protein is obtained at IFN concentrations lower than those that reduce cell killing by the virus. The immunoassay therefore provides a more sensitive measure for the IFN effect than that obtained by 'cytopathic effect inhibition' assays.

The basic steps of the assay of the invention are as follows:

Step I:

Suitable cells, such as cultured fibroblasts are cultivated to confluency in microwells. The sample to be assayed and a sample of known interferon (IFN) concentration are diluted serially and applied to such cell cultures in microwells.

Step II:

After a predetermined incubation time, the cells are infected with a suitable virus at a suitable concentration of same. VSF virus is suitable, and good results were obtained at a concentration of 10 pfu VSV per cell. The cells are further incubated in a suitable growth medium and at the end of the incubation period they are either frozen or lysed with a suitable detergent.

Step III:

The virus is lysed by adding a lysis buffer such as sodium desoxycholate buffer at pH of about 9.6. The lysed samples can be assayed or frozen for subsequent assaying.

Step IV: Quantitation of the viral protein yield:

Samples of the lysed viruses are transferred to radioimmunoassay or to ELISA microplates. Following incubation for 1–2 hours, the plates are then rinsed with Tween-PBS (0.05% Tween 20 (polyoxyethylene sorbitan monolaurate) in phosphate buffered saline). The quantitation is then continued, for example in one of the following ways:

a. The wells are incubated for 1 hr with anti-VSV serum, rinsed with Tween-PBS, incubated with $^{125}$I-labeled protein A ($10^5$ cpm per well) for 1 hr and rinsed with Tween-PBS (FIG. 6A); or b. The wells are incubated with anti-VSV serum as above, rinsed and incubated either with anti-IgG antibody or with protein A which has been conjugated to alkaline phosphatase and then ELISA is completed as in (FIG. 6B) or c. The cells are incubated with purified anti-VSV IgG, conjugated to alkaline phosphatase, in the presence of Tween-PBS, rinsed with Tween-PBS and incubated for 1 hour with color-producing substrate for the alkaline phosphatase, as in standard ELISA procedures (FIG. 6C). An example for the titration of IFN-γ on Wish cells, using procedures A(○) and C(●) is shown in FIG. 5. The IFN concentration causing reduction of the viral protein yield by 50% is, by definition, 1 unit/vol. Yet, as the IFN activity varies, depending on the type of cell used and its growth conditions, it is preferable to include a sample of known IFN concentration in the assay and to relate the activity of the tested samples to that exhibited by the sample of known concentration.

This assay can be applied for measuring the effect of IFN on a variety of other viruses using the specific anti-viral antibody.

DESCRIPTION OF THE DRAWINGS

The results obtained are summarized in the enclosed Figures, in which.

(A) Effect of Detergents.

Culture media of VSV-infected BSC-1 cells (□, ○) and non-infected (▲, ●) were diluted 1:1 in 0.1 M-sodium carbonate buffer pH 9.6, or in that buffer plus deoxycholate (○) or NP-40 (□) to the indicated final detergent concentration and incubated in the microwells of PVC immunoassay plates for 2 hrs at 37° C. The plates were then washed twice with PBS and twice with Tween-PBS and the amount of bound viral proteins was estimated by sequential incubation with anti-VSV antibody and iodinated Protein A.

(B) Dependence on Virus Concentration.

Twelve hrs after infection of BSC-1 cells ($2.5 \times 10^5$ cells in 2 ml growth medium) an equal volume of 0.5% deoxycholate in 0.1M-sodium carbonate buffer pH 9.6, was added either to the whole culture or just to the culture medium. The lysed samples were mixed in various proportions with samples of a similarly treated but non-infected culture and the extent of binding of the viral protein to the immunoassay plate, at the various dilutions of the virus, was determined as above. X=assay with culture medium; ● =assay with lysate of the whole culture.

Figure 2:
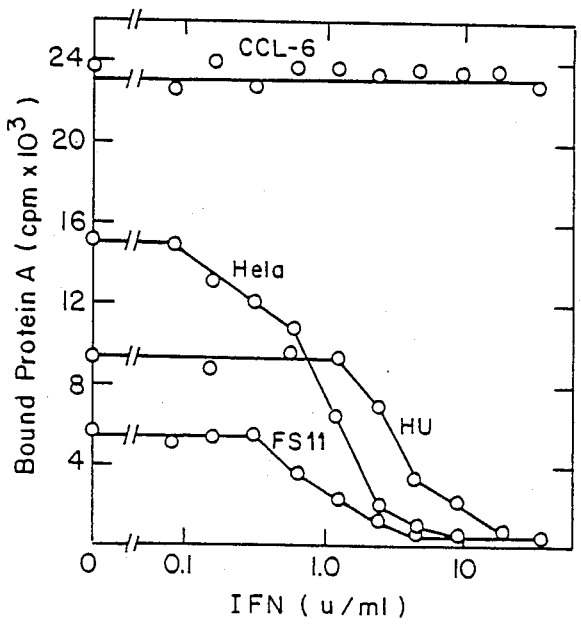

FIG. 2 illustrates the titration of IFN effect of VSV protein yield in various human cell lines. Cells were treated with human IFN-β for 24 hrs and then infected by VSV (10 p.f.u./cell). Twelve hours later, the infected cultures were lysed by deoxycholate and the virus protein content determined by radioimmunoassay. IFN concentration is presented in terms of antiviral activity on the HeLa cells, where 1 unit is defined as the concentration causing reduction of viral protein by 50%.

Figure 3:
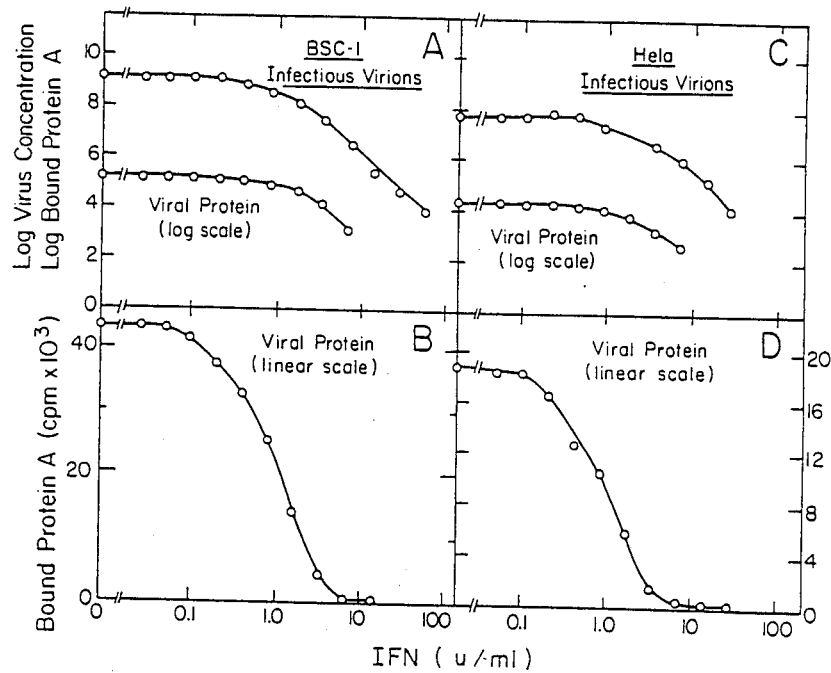

FIG. 3 illustrates the dose response of the IFN effect of VSV protein yield and on the yield of infectious virions. BSC-1 cells (a, b) were treated with IFN-α and HeLa cells (c,d) were treated with IFN-β for 24 hours and then infected for 12 hrs with VSV. The yield of infectious virions in the medium was determined by plaque assay on L-929 cells, and the yield of viral protein in the whole culture was determined by the radioimmunoassay. The yields of virus protein are presented in (a) and (c) on a logarithmic scale and in (b) and (d) on a linear scale, IFN concentration is presented in terms of antiviral activity in the two types of cell.

Figure 4:
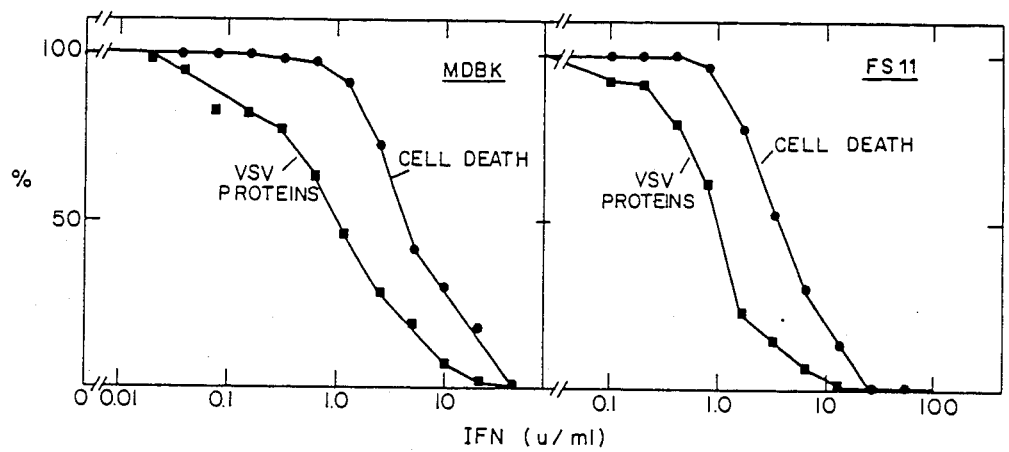

FIG. 4 illustrates the quantitative estimation of the relationship between the effect of IFN on viral cytopathy and its effect on viral yield. MDBK (a) and FS11 (b) cells were treated with various concentrations of IFN-β for 20 hrs, infected with VSV and further incubated for 20 hrs until cytopathic effect had developed in those cells not treated with IFN. The yield of viral protein in the culture and the decrease of neutral red dye uptake by the cell, as an indication of cell death, were then determined in parallel. Viral protein yield (■) is expressed as a percentage of its level in the absence of IFN, and the decrease in neutral red uptake (●) as a percentage of the dye taken up by non-infected culture. IFN concentration is presented as in FIGS. 2 and 3. A similar dissociation between the effect of viral cytopathy and on protein yield was observed with IFN-α (not shown).

Figure 5:
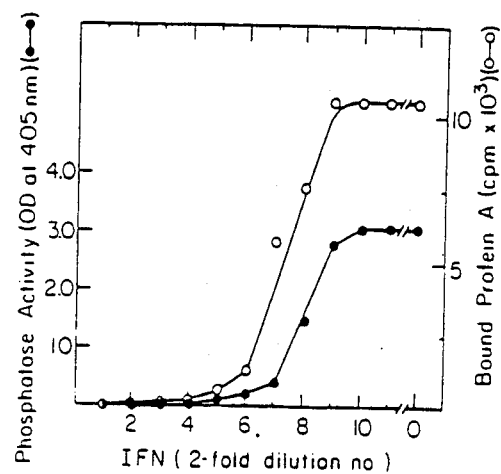

FIG. 5 compares titration of IFN by measuring VSV protein yield either by radioimmunoassays ( ) or by ELISA (●). The first illustrated in FIG. 6A and the second in FIG. 6B.

Figure 6:
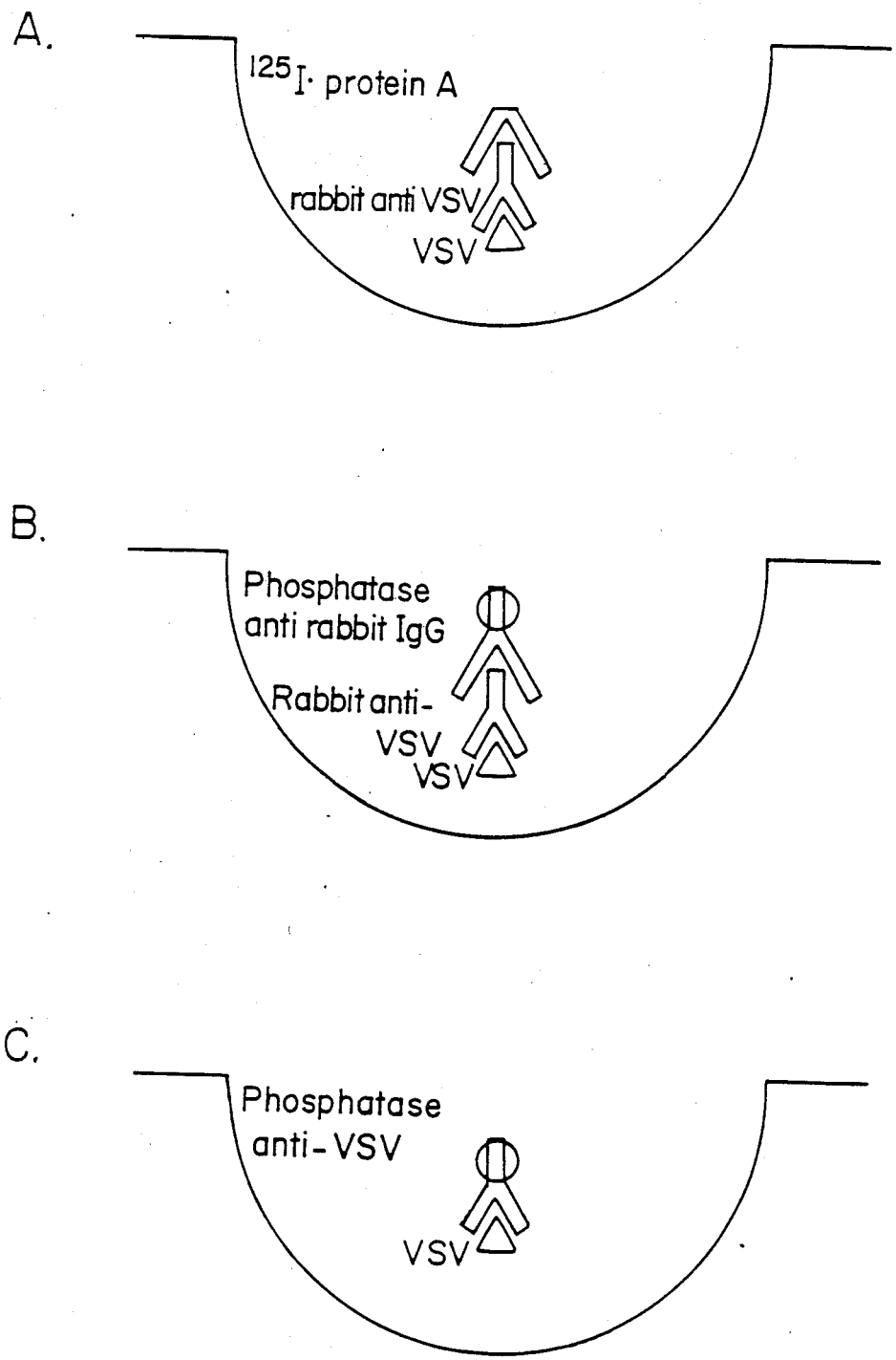

FIG. 6 illustrates alternative procedure of immunoassays of VSV proteins.

DESCRIPTION OF THE PREFERRED EMBODIMENT

The invention is illustrated by way of example with reference to the following detailed example, which is given by way of illustration only.

EXAMPLE

Cells. The human cell lines used in this study were: HU obtained from the Hadassah University Hospital, Jerusalem, CCL-6 obtained from the American Type Culture Collection and HeLa obtained from Flow Laboratories. FS11 is a strain of human foreskin fibroblasts, established in our laboratory.

In addition there were monkey BSC-1 fibroblasts, bovine MDBK cells, baby hamster kidney (BHK) cells and mouse L-929 cells. All cells were grown in Dulbecco's modified Eagle's medium in the presence of 10% foetal calf serum (FCS).

VSV and antiserum against its proteins: VSV of the Indiana serotype was re-cloned several times in BSC-1 cells and used at a low passage number. Virions, produced either in BSC-1 cells or in a spinner culture of BHK cells, were purified on a sucrose gradient and on a tartrate-glycerol gradient, as previously described (Wallach & Revel, 1980). Rabbits were injected intramuscularly with 0.5 mg of purified virions emulsified in complete Freund's adjuvant and 5 months later with a further 2 mg injected by the same route, as well as 0.5 mg u.v.-irratiated virions supplied intravenously. A month later, the animals were again injected intramuscularly with 0.5 mg of purified virions which had been lysed in 0.5% Nonidet P40(NP40), fixed in 3% formaldehyde and, after extensive dialysis, mixed with complete Freund's adjuvant. The rabbits were bled a week later. The titre of antibodies in the sera was found to be saturating in the solid-phase immunoassay at a dilution of up to 1:200.

IMMUNOASSAY OF VIRUS PROTEINS AND QUANTIFICATION OF THE IFN EFFECT

Treatment with IFN. Cells were seeded in microwells at concentrations of $2.5 \times 10^5$ cells in 18 mm microwells or $3.50 \times 10^4$ cells in 9 mm microwells. A few hours later, serial dilutions of the solutions to be tested and IFN samples of known concentrations were applied to the cells.

Infection by the virus. Twelve to twenty-four hrs after application of IFN, growth medium was removed from the cells and the virus was applied in growth medium containing 2% FCS, at a multiplicity of 10 p.f.u./cell(50 μl/microwell). Several cell samples were incubated without virus and other with virus but without pretreatment by IFN. Two hrs after application of the virus, the virus-containing growth medium in the micro wells was replaced by a fresh medium containing 10% FCS (100 μl/microwell) and the cells were incubated for a further 10 to 20 hrs. The infected cultures were kept frozen before further processing for the assay of the virus proteins. Optimal duration of incubation with the virus could be estimated by observing the development of virus cytopathic effect.

Transfer of the VSV proteins. The virus protein was first solubilized by adding to the culture medium an equal volume of a soltuion of 0.5% sodium deoxycholate in 0.1M-sodium carbonate buffer, pH 9.6. Lysis of the cells by the detergent could be hastened by incubation at 37° C. for about 20 min. Fifty μl aliquots of the solubilized protein were then transferred to V-shaped microwells in PVC radioimmunoassay plates (Dynatech 1-220-25) using a 'Titertek', multichannel pipette.

Immunoradiometric assay. The PVC plate was incubated for 2 hrs in a humidified chamber at 37° C. Non-adsorbed protein was rinsed off with a solution of 0.05% Tween-20 in phosphate-buffered saline (Tween-PBS). Anti-VSV antiserum, diluted in Tween-PBS, was then applied in a volume of 20 μl to each well and the plate was incubated again for 2 hrs at 37° C. After rewashing with Tween-PBS, the plate was incubated for 1 h at 37° C. with $^{125}$I-labelled Protein A (20 μl, $5 \times 10^6$ ct/min per ml of 1% bovine serum albumin in PBS). The plate was then washed with Tween-PBS and the amount of label adsorbed to each well was determined in a γ-counter. Control values (usually less than 5%) were subtracted.

Definition of the unit of antiviral activity. We refer here to a unit of IFN as that amount which, when present in 1 ml, gives 50% reduction in virus yield. The concentrations of IFN necessary to cause a reduction in virus yield are shown in this study to be significantly lower than those causing reduction of virus cytopathic effect. Since the latter parameter is widely used to quantify FN, concentrations referred to as 1 U/ml in this study might be lower than in many others. Indeed, we found that the currently available international standards for both IFN-α (NIH G 023-901-527) and IFN-β (NIH G-023-902-527) cause a 50% reduction in VSV protein binding at concentrations lower than those defined by there producers as 1 U/ml (at 0.43 U/ml IFN on MDBK cells and at 0.24 U/ml IFN-α on human foreskin fibroblasts).

Quantification of cytopathic effect by neutral red uptake. The assay was performed as described by Finter (1969) J. Gen. Virology, 5, 414–427. Materials. IFN-β was induced by poly(rI) poly(rC) in FS11 cells and partially purified on a DEAE-Sephadex column. IFN-α was induced in Namalwa lymphoblastoid cells by Sendai virus and partially purified by adsorption to immobilized anti-interferon antibody. Protein A was purchased and iodinated with Bolton-Hunter reagent or obtained in the labelled form. Tween-20 was obtained commercially.

Figure 1:
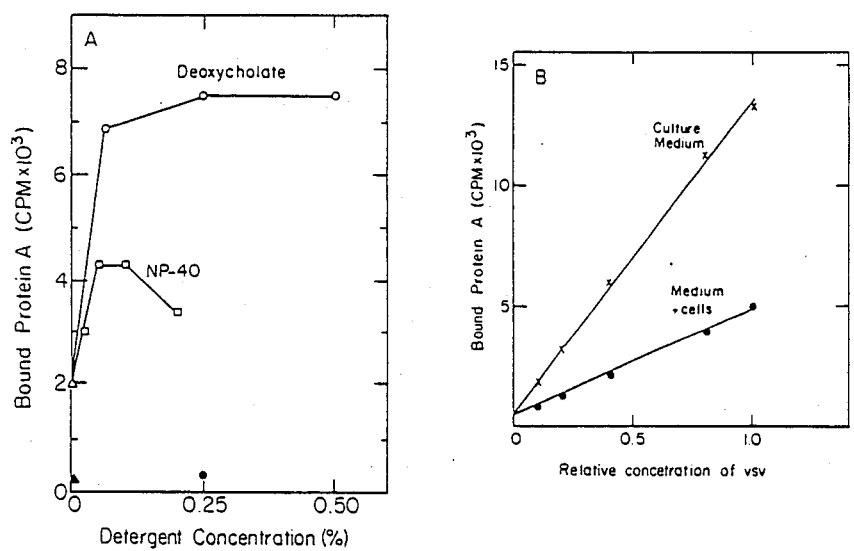
FIG. 1 illustrates the binding of VSV protein to the immunoassay plate.

Low binding of virus protein to PVC plates observed after incubation with cell growth medium which contained virus could be significantly enhanced by adding detergents to the virus suspensions (FIG. 1a). Comparison of several detergents suggested a correlation between an increase in binding to the PVC and the effectiveness of the detergent in dissociating the proteins of VSV. Thus, deoxycholate which causes release of both of the G and M proteins of VSV and a disruption of the viral nucleocapsid (Cartwright et al., 1970 J. of Gen. Virology 7, 19–21 and 7, 267) was significantly more effective than NP40, which is known to release selectively only the G protein (FIG. 1a). Apparently, the effect of deterent on adsorption of the virus proteins to PVC is primarily a reflection of an increase in the availability of these proteins as a result of disruption of the virus membrane and ribonucleoprotein core.

There was a linear correlation between the amount of virus proteins that adsorbed to the plates and their concentration in the tested sample (FIG. 1b). This binding formed the basis for a simple immunoassay for the virus protein which involved mixing the virus-containing sample with detergent solution, transferring a sample of the mixture to a PVC plate and then quantifying the virus protein which was bound to the PVC plates by sequential incubation with anti-VSV serum and $^{125}$I-labelled Protein A. The serum protein, present in rather high amounts in the cell growth medium, could not fully prevent binding of virus proteins to the PVC plates. The amount of virus protein formed within 2 hrs of infection was, in cells of various human (FIG. 2), monkey (FIG. 3), bovine (FIG. 4), and mouse cell lines (not shown), high enough to be quantified by this immunoassay. While initially this procedure was used for measuring the amount of virus protein in the growth medium of infected cells, we found it later convenient to add deoxycholate directly to the whole infected culture. The detergent lysed the cells and thus permitted measurement of the total amount of virus protein in the culture. The efficiency of binding virus protein to PVC in the presence of cell lysate appears to be lower than it its absence, probably due to competition of some cellular proteins with the virus proteins, for binding sites on the PVC (FIG. 1b, compare binding with culture medium to binding with medium plus cells). This competition, however, did not interfere with the assay since even in the presence of cell lysate the binding of virus protein to PVC was linearly proportional to their concentration (FIG. 1b).

As seen in FIG. 2, cells of various lines showed substantially reduced yields of virus protein after treatment with IFN. Comparison of the decrease in virus protein with the decrease in production of infectious virions, as measured by the plaque assay, showed that both responded similarly to IFN. The minimal IFN concentration at which the antiviral effect could be detected was about the same for the decrease of virus proteins and the decrease of infections virions (FIG. 3), Nevertheless, this comparison shows a clear advantage of the immunoassay over the plaque assay for measuring the antiviral effect at very low concentrations of IFN. The decrease of virus yield by a few percent at such IFN concentration is much simpler to quantify accurately by the immunoassay than by the plaque assay. On the other hand, the immunoassay is clearly not applicable for measuring the antiviral effect of very high concentrations of IFN since it allows the quantification of viral proteins only at virus concentrations higher than about $10^6$ p.f.u./ml (FIG. 3)

On examining the morphology of the infected cells it was observed that protection from killing by the virus could only be detected with IFN concentrations higher than those causing a reduction in viral protein. To confirm this observation there was quantified the viral cytopathy by measuring the neutral red uptake capacity of the cells. Comparison of the yield of viral protein and the extent of vital cytopathy showed a more effective response of the former parameter to IFN (FIG. 4). At a low concentration of IFN, effective reduction of viral protein while no decrease of cell viability could be observed.

DISCUSSION

The immunoassay for measuring the yield of virus protein provides a sensitive and quantitative tool for estimation of the antiviral effect of IFN. In several respects it is preferable to the 'cytopathic effect inhibition' assay which is now the method most widely applied for measuring the action of IFN; it gives a more direct quantification of the change induced by IFN and it is independent of the morphological response to the virus; in fact, it can even serve for estimating the effect of IFN on viruses which are not cytopathic at all, providing that antibodies against their proteins are available.

An interesting phenomenon revealed when comparing the sensitivity of the immunoassay and of the cytopathic effect assay is a difference in the IFN concentration dependence of the reduction in virus yield and in virus cytopathic effect. This difference is probably due to the existence of excess constituents of the virus in the infected cell, beyond the minimal amount necessary to cause destruction. Another factor which might have contributed to this phenomenon is the ability of IFN to induce increased sensitivity of the cells to virus cytopathy. This difference in IFN concentration dependence implies that the immunoassay gives a more sensitive indication of the antiviral effect than that provided by the cytopathic effect inhibition assay. There are a number of different ways whereby solid-phase immunoassay can be performed. Steps can be taken to permit sensitive detection of very low quantities of antigen either by its enrichment, using plates which have been pre-coated with antibody ('sandwich' technique) or by using a highly labelled sample of antigen (competition radioimmunoassay). Yet the large amounts of VSV proteins found in infected cells, and their effective binding to PVC, allows their quantification by a very simple, direct immunoassay. A major attractive feature of this technique is that the amount of bound antigen is linearly proportional to its concentration in the culture, over a wide range of concentrations. It is therefore not necessary to dilute the samples before the test.

Although there are known many different effects of IFN on cell functions, none is as ubiquitously observed and as specific to IFN as the antiviral effect.

A KIT FOR THE ASSAY

A kit by which the assay can be applied in any laboratory, which is equipped for tissue culture, will include the following components:

(1) A lyophilized sample of virus.

(2) Concentrated lysis buffer (sodium deoxycholate in sodium carbonate buffer).

(3) Concentrated Tween-PBS Buffer.

(4) One of the following alternative agents:

(a) Purified anti-VSV immunoglobulin (or monoclonal antibody against the M Protein of VSV) coupled to alkaline phosphatase or to another enzyme which is in use for ELISA; or (b) Anti-VSV serum and $^{125}$I-labelled Protein A; or (c) Anti-VSV serum and enzyme coupled anti-IgG serum.

When using chôices (a) or (c) the kit will also include the substrate for the enzyme, used in the ELISA, and a stopping solution which terminates the cleavage of this substrate by the enzymer.

(5) Microplates for ELISA (choice (a) or (c)) or for radioimmunoassay (choice b).

We claim:

1. A process for the determination of interferon (IFN) which comprises cultivating cells by tissue culture, applying to such cell culture a sample of the IFN to be measured, infecting the cells with a virus, incubating same for a predetermined period of time, lysing the virus by application of a detergent, and assaying the lysed samples for virus protein content.

2. A process according to claim 1, wherein the virus used is vesicular stomatitis virus (VSV).

3. A process according to claim 1, wherein the virus-infected cell cultures are lysed and applied to vessels of PVC.

4. A process according to claim 3, wherein the vessels are PVC microwells.

5. A process according to claim 3, wherein the resulting PVC-bound protein is incubated with anti-VSV antibody, and the absorbed IgG is measured.

6. A process according to claim 1, wherein the lysed viruses are quantitated by a radioimmunoassay or by the ELISA type assay.

7. A process in accordance with claim 1, wherein said cells are cultured fibroblast cells.

8. A process according to claim 1, wherein said virus is vesicular stomatitis virus (VSV) and said assaying step comprises applying the virus infected cell cultures to to vessels of polyvinyl chloride (PVC) and quantifying the resulting PVC-bound protein by radioimmunoassay or by the ELISA-type assay.

9. A process in accordance with claim 8, wherein said quantifying step comprises incubating the PVC-bound protein with anti-VSV antibody and measuring the adsorbed antibody.

10. A kit for carrying out an assay of IFN, comprising in combination:

a. Lyophilized virus sample;

b. Lysis buffer;

c. Assay buffer;

d. One of the following:

(i) purified anti-virus immunoglobulin coupled to an enzyme usable for ELISA, or (ii) anti-virus serum and enzyme-coupled anti-IgG serum;

e. A substrate for the enzyme used in the ELISA;

f. A stopping solution which terminates the cleavage of the substrate by the enzyme, and g. Microplates for ELISA.

11. A kit in accordance with claim 10, wherein said lyophilized virus sample is a sample of lyophilized vesicular stomatitis virus. (VSV).

12. A kit in accordance with claim 10, wherein said microplates have an interior of polyvinyl chloride.

13. A kit for carrying out an assay of IFN, comprising in combination:

a. Lyophilized virus sample;

b. Lysis buffer;

c. Assay buffer;

d. Anti-virus serum and $^{125}$I-labelled Protein A; and e. Microplates for radioimmunoassay.

14. A kit in accordance with claim 13, wherein said lyophilized virus sample is a sample of lyophilized vesicular stomatitis virus (VSV).

15. A kit in accordance with claim 13, wherein said microplates have an interior of polyvinyl chloride.

* * * * *